(12) United States Patent
Wallis et al.

(10) Patent No.: US 6,884,412 B1
(45) Date of Patent: Apr. 26, 2005

(54) DECTECTION OF AND METHODS AND COMPOSITION FOR PREVENTION AND/OR TREATMENT OF PAPILLOMATOUS DIGITAL DERMATITIS

(76) Inventors: Dale Wallis, 1785 E. Main St. #4, Woodland, CA (US) 95776; James L. Wallis, 1785 E. Main St. #4, Woodland, CA (US) 95776

( * ) Notice: Subject to any disclaimer, the term of this patent is extended or adjusted under 35 U.S.C. 154(b) by 0 days.

(21) Appl. No.: 09/670,421

(22) Filed: Sep. 26, 2000

Related U.S. Application Data

(62) Division of application No. 08/903,559, filed on Jul. 31, 1997, now Pat. No. 6,162,429.
(60) Provisional application No. 60/022,915, filed on Aug. 1, 1996.

(51) Int. Cl.$^7$ .......................... A01N 63/00; A01N 65/00
(52) U.S. Cl. ..................... 424/93.1; 424/93.3; 424/93.4
(58) Field of Search ............................... 424/93.1, 93.3, 424/93.4

(56) References Cited

U.S. PATENT DOCUMENTS

| | | | |
|---|---|---|---|
| 3,607,909 A | * | 9/1971 | Beregi et al. |
| 3,673,205 A | * | 6/1972 | Spicer et al. ............... 548/154 |
| 4,029,763 A | | 6/1977 | Kilbourne |
| 4,587,254 A | * | 5/1986 | Toyofuku et al. ........... 514/326 |
| 4,879,213 A | * | 11/1989 | Fox |

OTHER PUBLICATIONS

Plotkin et al *VACCINES* W.B. Saunders Co. Philadelphia, PA p. 571, 1988.*
Hespell (International Journal of Systematic Bacteriology vol. 27(4) pp 371–381), Oct. 1977.*

Hickman, C.P. Sr. et al., *The C.V. Mosby Company,* p. 29, "Integrated Principles of Zoology" (1979).

Jawetz, E. et al., *Appleton & Lance,* Chapter 11, p. 168, "Review of Medical Microbiology" (1987).

Keeton, T., *W. W. Norton & Co.,* 3d Ed., p. 41, "Biological Science" (1980).

Langone, J.J., *Academic Press,* vol. 178, pp. 375–390, 746–764, "Antibodies, Antigens, and Molecular Mimicry" (1989).

Martin, D. W., *Lange Medical Publications,* 18$^{th}$ Ed., p. 7, "Harper's Review of Biochemistry" (1981).

Sigma, pp. 2172–2173, "Biochemicals and Reagents for Life Science Research" (2002–2003).

Stites, D.P. et al., *Appleton & Lange,* 7$^{th}$ Ed., p. 131; "Basic and Clinical Immunology".

Tizard, I.R. et al., *W.B. Saunders Company,* 6$^{th}$ Ed., Chapter 2, p. 10, Chapter 3, p. 21; "Veterinary Immunology".

Tortora, G.J. et al., *The Benjamin/Cummings Publishing Company,* Chapter 15, pp. 382–383, "Microbiology" (1982).

Wisdom, G.B., *Oxford University Press,* "Peptide Antigens" (1994).

\* cited by examiner

*Primary Examiner*—Mark Navarro
(74) *Attorney, Agent, or Firm*—McDonough Holland & Allen PC

(57) ABSTRACT

The present invention relates to the use of *Serpens* spp. bacteria or bacterin in compositions, such vaccines, and methods for the detection, prevention and/or treatment of Papillomatous Digital Dermatitis in ruminants. The present invention also provides biologically pure *Serpens* spp. strain HBL-112, and biologically pure *Serpens* spp. strain HBL-112 bacterin.

2 Claims, 7 Drawing Sheets

# DECTECTION OF AND METHODS AND COMPOSITION FOR PREVENTION AND/OR TREATMENT OF PAPILLOMATOUS DIGITAL DERMATITIS

This application is a divisional of U.S. application Ser. No. 08/903,559, filed Jul. 31, 1997, now U.S. Pat. No. 6,162,429, which claims benefit of U.S. Provisional Application No. 60/022,915, filed Aug. 1, 1996.

FIELD OF THE INVENTION

The present invention relates to methods and compositions useful in the detection, prevention and/or treatment of papillomatous digital dermatitis is ruminants and to a novel strain of Serpens spp. bacteria useful for that purpose.

BACKGROUND OF THE INVENTION

Papillomatous Digital Dermatitis (PDD) is a chronic infectious and apparently contagious disease of the feet and/or lower legs of cattle. The disease is known by several common and scientific names including digital dermatitis, interdigital papillomatosis, digital papillomatosis, verrucous dermatitis, footwarts, hairy footwarts, hairy heelwarts, raspberry heel, strawberry foot disease and strawberry footrot. It has been identified as one of the most significant diseases facting the diary industry today. The disease results in lameness which leads to economically significant reductions in milk production and concomitant declines in animal health such as body weight loss, and fertility. It is believed that the agent can be brought onto a diary via introduction of new stock or formite transmission from hoof trimmers, dairy testers, muddy boots on veterinarians, etc. In dairies currently experiencing losses from the disease, it has been estimated that the cost in lost milk production, reproductive losses and increased culling averages at least $100 per day.

To date, only two control methods have shown promise: use of antibiotics topically (cleaning, curettage and bandaging each foot) or parenterally (problematic for reasons of milk withdrawal), and the use of bacteriocidal footbaths (antibiotics, formaldehyde, iodine, etc.). Although many lesions may respond well to antibiotics or footbaths containing antibacterial compounds, recurrences are known to occur and some evidence suggests development of antibiotic resistance. These approaches are labor intensive, prone to human error, costly (antibiotics for 30 days of footbaths runs $2,500 for a 400 cow dairy), subject to governmental restrictions, and do not confer either environment cleanup or lasting protection from recurrence.

In view of the significant economic damage caused by PDD, an effective way to detect and treat animals infected with the disease, as well as a means to protect them against future infection, is highly desirable.

SUMMARY OF THE INVENTION

The present invention relates to compositions and methods for the detection, prevention and/or treatment of Papillomatous Digital Dermatitis in ruminants.

The present invention now provides a method of preventing and/or treating Papillomatous Digital Dermatitis in ruminants comprising administering to the ruminant a therapeutically effective amount of Serpens spp. bacteria or Serpens spp. bacterian and/or an immunologically active portion thereof and/or an antigenic epitope cross-reactive with Serpens spp.

The present invention further comprises a pharmaceutical composition for preventing and/or treating Papillomatous Digital Dermatitis in ruminants comprising a therapeutically effective amount of Serpens spp. bacteria or Serpens spp. bacterin and/or an immunologically active portion thereof and/or an antigenic epitope cross-reactive with Serpens spp. and a veterinerally acceptable diluent or carrier.

The present invention further comprises a method of determining the presence of PDD antibodies in a sample of ruminant serum comprising contacting the sample with an antigen selected from the group consisting of bacteria or bacterin of the Serpens genus or an immunologically active portion thereof and/or an antigenic epitope cross-reactive with Serpens spp. and detecting and antibodies in the sample which bind to the antigen. The present invention can also be used to determine the presence of PDD antigen or anti-Serpens spp. antibodies.

The present invention further comprises the use of a diagnostic kit for determining the presence of PDD antibodies wherein the kit comprises an antigen and one or more binding partners.

The present invention also provides biologically pure Serpens spp. strain HBL-112, and biologically pure Serpens spp. strain HBL-112 bacterin. Serpens spp. strain HBL-112 bacteria Deposit No. 1 and Serpens spp. strain HBL-112 bacterin Deposit No. 2 has been deposited at Hygieia Biological Laboratories at Post Office Box 8300, Woodland, Calif., 95776. Serpens spp. strain HBL-112 is a member of the Serpens spp. genus and has the biological and morphological characteristics defined below.

BRIEF DESCRIPTION OF THE DRAWINGS

The present invention is illustrated by the following drawings, in which.

DETAILED DESCRIPTION OF THE INVENTION

Figure 1:
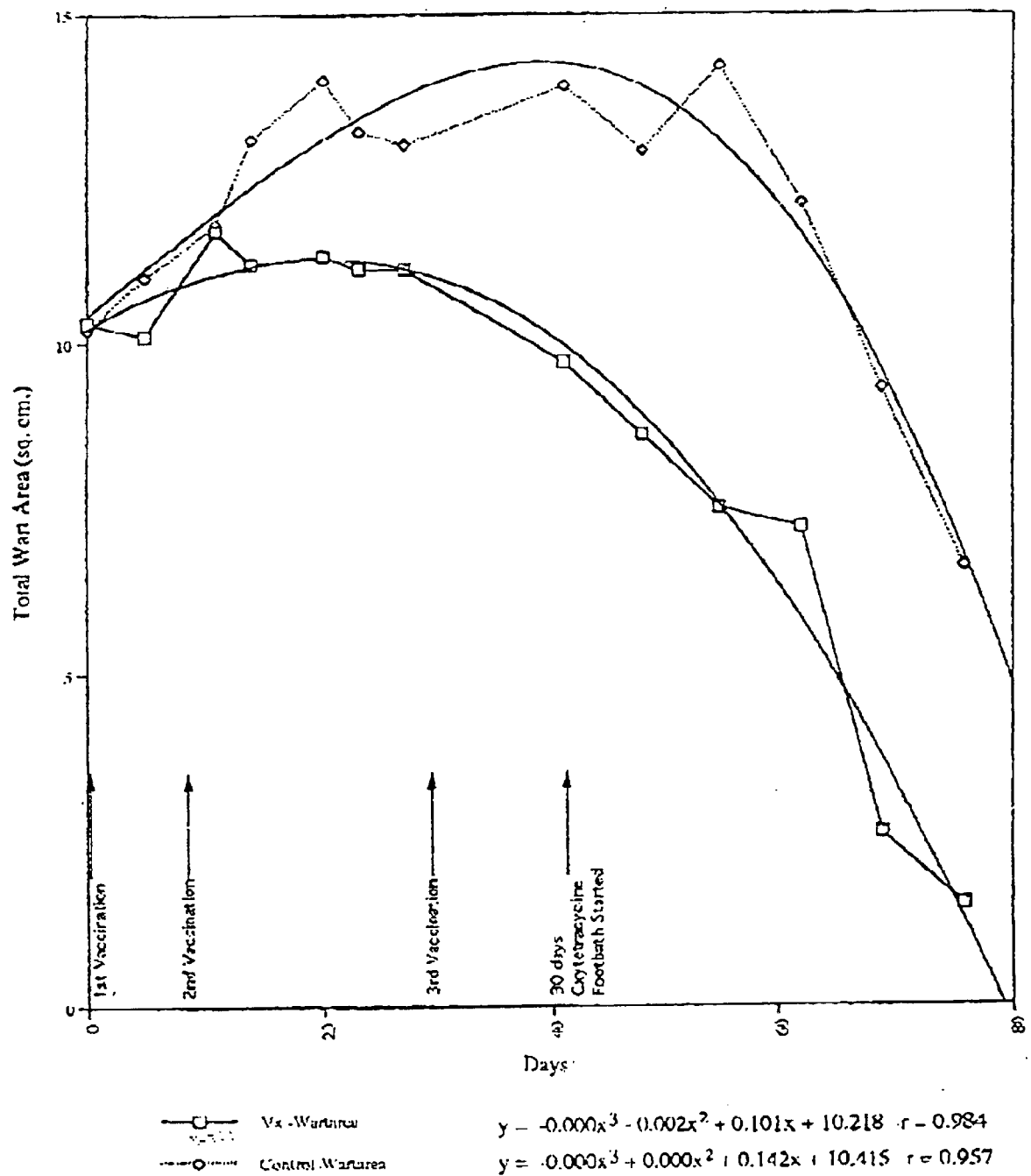
FIG. 1 is a graph showing the clinical reduction in total footwart area seen in dairy cattle with preexisting footwarts in response to vaccination using Serpens spp. strain HBL-112 bacterin, according to the present invention as compared to a control. Wart area is given in square centimeters, calculated from millimeter measurements made in two dimensions of the lesions on the feet of clinically affected cattle. Time is shown as days after enrollment in the trial. Total elapsed time is 76 days.

Isolation and Purification of Serpens spp. strain HBL-112

Prior to the present invention, the only known species of the genus Serpens were Serpens flexibilis which was isolated from the upper centimeters of sediment (mud) found in eutrophic freshwater ponds. *S. flexibilis* are rod-shaped cells, 0.3–0.4 µm wide by 8–12 µm long. They occur singly or in pairs. Cells in the stationary phase of growth are longer and often possess blebs or spherical protuberances. *S. flexibilis* has a uniquely flexible motion. They process bipolar tufts of 4–10 flagella and also a few lateral flagella. None of the published literature on this organism indicates any proclivity for pathogenesis, nor even any association with animals.

*Serpens* spp. strain HBL-112 was isolated by the present inventors from wart tissue of cattle suffering from PDD. The wart tissue was minced and filtered into liquid media as well as by direct inoculation into wells cut into soft agar plates. Incubation of parallel cultures was accomplished at 25–37° C. under a variety of atmospheres, such as, 10% $CO_2$ (candle jar), aerobic, anaerobic and microaerophilic (CampyPak). Final purification of the strain was accomplished by alternate passage between soft agar (0.8%) and standard agar (1.5–2%) plates.

An alternative method for isolating *Serpens* spp. strain HBL-112 is to mince the wart tissue, place it upon a filter disk (0.45 µm pore size) on a soft agar plate, and incubate it for 2–6 hours under decreased oxygen conditions (candle jar). Removing the filter disk after a short incubation reduces the risk of contamination by swarmers able to swim across the disk but not through it. Using a lowered agar concentration in the agar plate permits rapidly swimming spirochetes (and *Serpens* spp.) to move through the agar away from lesser mobile bacteria, becoming purified. Repeated sequential passages through the filter/soft agar results in a purified bacterial culture, whether the bacteria is a spirochete or *Serpens* species, such as *Serpens* spp., strain HBL-112.

The rate of movement through the soft agar can be used to distinguish between spirochetes and *Serpens* spp. In very soft agar (0.5% *Serpens flexibilis* moves 4 mm/hour, reaching the edge (from the center) of a 100 mm agar plate in approximately 12 hours while very fast spirochetes move only 0.5 to 0.8 mm/hour. In soft agar (0.8%), *S. flexibilis* moves 2 mm/hour, while *Serpens* spp. strain HBL-112 moves approximately 1.5 mm/hour.

Microscopic Morphology and Motility

Figure 5:
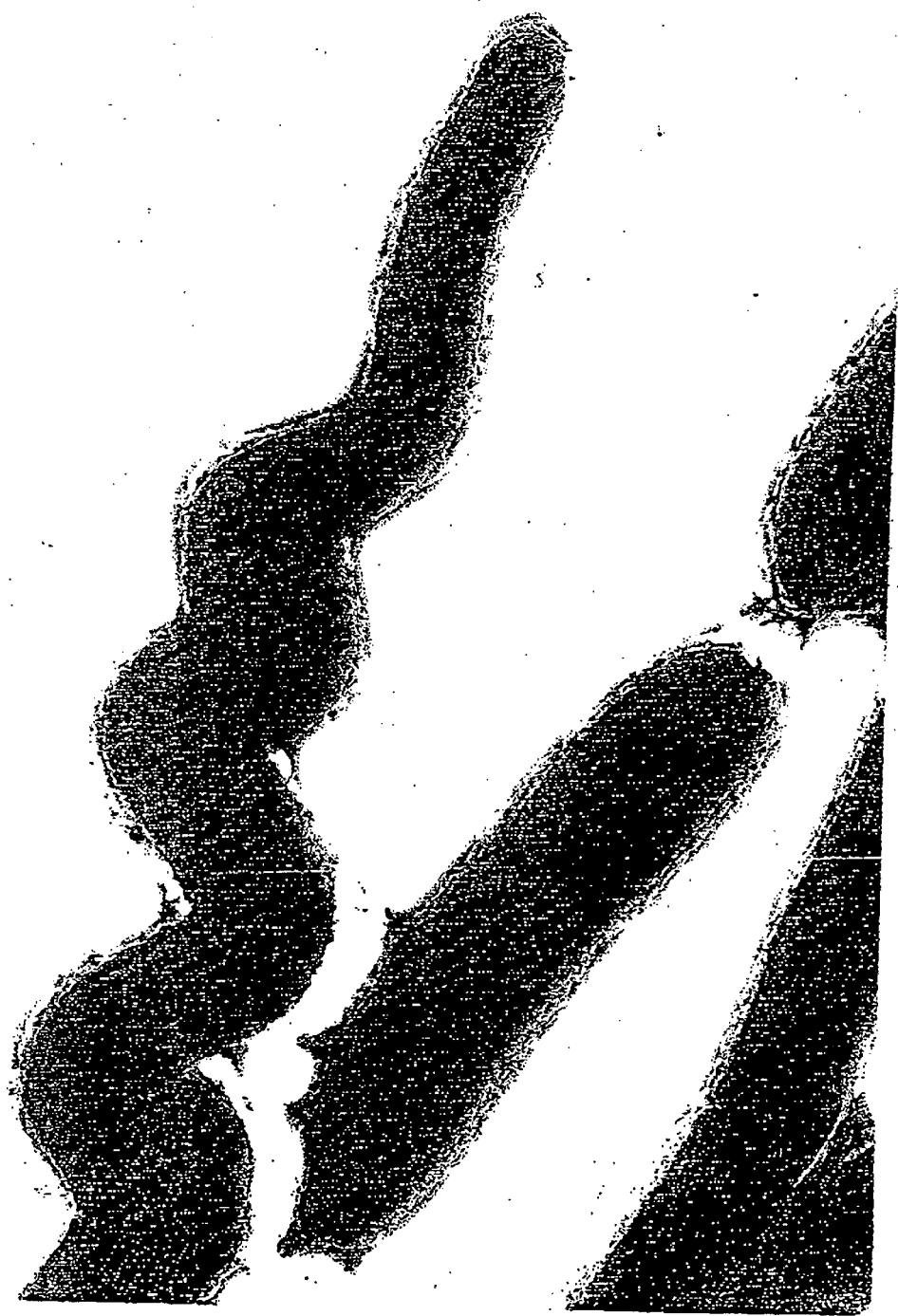
FIG. 5 is a photomicrograph illustrating the inducible spiral form of Serpens spp., strain HBL-112.
Figure 6:
FIG. 6 is a photomicrograph of the same pure culture Serpens spp. strain HBL-112 as FIG. 5 showing the long rods, short rods and spherical bodies typical of the Serpens genus.

Light microscopy of *Serpens* spp. strain HBL-112 reveals a poorly staining gram negative rod, often curved, with typically 0.5% to 5% of the cells (up to 100% depending upon media constituents and growth conditions) demonstrating rigid spirals (FIG. 5). As shown in FIG. 6, the *Serpens* spp., strain HBL-112 bacteria are highly pleomorphic, with three main forms seen: straight or curved roots, "polliwogs" or spherical cyst-like structures, and rigid spirals. Rods may or may not have sections of rigid spirals interspersed with straight sections. Variations in growing conditions will induce a greater preponderance of one or another form seen under "standard" conditions.

Wet mount phase contrast microscopy of *Serpens* spp., strain HBL-112 curved and straight rods on the cut edge of a soft agar block reveals the unique and characteristic flexing and serpentine motility reported for *Serpens flexibilis*. The rods, but not the polliwod or rigid spiral forms, demonstrate a swimming to serpentine motion, with the serpentine motion and flexibility especially evident under higher viscosity conditions. Direction reversal is rapid, with organisms capable of movement in either direction along their longitudinal axis. Rigid spirals often appear nonmotile. "Polliwog" and cyst forms display a swimming/wriggling motility similar to true polliwogs. Using wet mount slides taken from standard agar plates, the morphology of young cultures is predominantly rods. Older cultures exhibit vastly differing rod forms, as well as coccoid and polliwog forms.

With the "soft" agar medium, *Serpens* spp. are observed by cutting a small agar block out and dicing it onto the slide. *Serpens* spp. which are observed within the agar or in contact with it exhibit the serpentine motility. *Serpens* spp. which are washed away from the agar are generally in the rod form, although they exhibit flexing and a spiral-like motility.

A rigid spiral form of *Serpens* spp. strains HBL-112, as shown in FIG. 5, occurs rarely in many media, but becomes more frequent in media containing higher concentrations of sulfur compounds such as cysteine and thioglycollate. When these compounds are added in even higher concentrations, the organism can be converted to nearly 100% spiral form.

Figure 7:
FIG. 7 is a photomicrograph of the same pure culture of Serpens spp. strain HBL-112 as FIG. 5 showing flagella associated with Serpens spp. strain HBL-112.

Transmission electron microscopy confirms the three predominant morphological phenotypes. Axial filaments (flagella lying adjacent to the bacterial cell, within a cell membrane) characteristic and essential for identifying an organism as a spirochete, are not present in *Serpens flexibilis* nor in *Serpens* spp., strain HBL-112. Flagella are seen attached terminally on some of the straight and curved rods, and also along the sides of the organism (lateral flagella); the number of flagella on each end (terminal or subterminal) is expected to be approximately 2–4 as shown in FIG. 7.

Biochemistry

Biologically pure *Serpens* spp., strain HBL-112 of the present invention and *Serpens flexibilis* were characterized by the standard biochemical reactions reported in Tables 1a and 1b below. Table 1a presents data on the biochemical reactions of *Serpens flexibilis*, *Serpens* spp., strain HBL-112, of the present invention, as well as three bacterial genera thought to be closely related to the *Serpens* genus, which currently remain unassigned to a bacterial Family according to Bergery's Manual of Determinative Bacteriology.

Table 1b presents data on the enzyme reactions of *Serpens flexibilis*, *Serpens* spp., strain HBL-112, two spirochete strains proposed by CVDLS (California Veterinary Diagnostic Laboratory System) as possible etiological agents for PDD, and a broad sampling of spirochete genera related to the two CVDLS spirochete strains. The "CVDLS isolate" is actually seven strains of spirochete isolated in conjunction with hairy footwart lesions, all having the same enzyme reactions. CVDLS 1-9185 MED is an eighth strain of spirochete which has a different enzyme profile than the other CVDLS isolates.

TABLE 1a

Summary of Biochemical Reactions

| Biochemical Reaction | HBL #112 Serpens spp. | ATCC 29606 S. flexibilis | Pseudo- monas spp. | Alcaligenes spp. | Vibrio hollisae |
|---|---|---|---|---|---|
| ONPG | – | – | – | – | – |
| Arginine dihydrolase | – | – | – | – | – |
| Lysine Decarboxylase | – | – | – | – | – |
| Ornithine Decarboxylase | – | – | – | – | – |
| Citrate as sole C-source | – | – | – | – | – |
| H2S Production | – | – | – | – | – |
| Urea hydrolysis | – | – | – | – | – |
| Tryptophan deaminase | – | – | – | – | – |
| Indole Production | – | – | – | – | + |
| VP | –+ | – | – | – | |
| Hydrolyzes Gelatin | – | – | + | – | – |

TABLE 1a-continued

Summary of Biochemical Reactions

| Biochemical Reaction | HBL #112 *Serpens* spp. | ATCC 29606 *S. flexibilis* | *Pseudomonas* spp. | *Alcaligenes* spp. | *Vibrio hollisae* |
|---|---|---|---|---|---|
| Ferments: | | | | | |
| Glucose | − | − | − | − | − |
| Mannose | − | − | − | − | − |
| Inositol | − | − | − | − | − |
| Soroitol | − | − | − | − | − |
| Rhamnose | − | − | − | − | − |
| Saccharose | − | − | − | − | − |
| Melibiose | − | − | − | − | − |
| Amygdalin | − | − | − | − | − |
| Arabinose | − | − | − | − | + |
| Oxidase | + | + | + | + | + |
| Reduces nitrate to nitrite | + | + | + | + | + |
| Reduces nitrite to nitrogen | − | + | − | − | − |
| Motility | + | + | + | + | + |
| Catalase | + | + | N* | N | N |

*N = not available

As shown in Table 1a, *Serpens* spp. strain HBL-112 of the invention is very weakly catalase positive by peroxide, oxidase positive by spot oxidase testing (Difco Spot-test), and gives the following reactions after forty-eight hours of incubation (at 35–36° C.) on API 20E strips (bioMérieux): negative for ONPG (o-nitrophenyl-β-D-Galactopyranoside), negative for arginine dihydrolase, negative for lysine decarboxylase, negative for ornithine decarboxylase, does not use citrate, does not produce hydrogen sulfide from thiosulfate, negative for urease, negative for tryptophan deaminase, does not form indole from tryptophan, does not produce acetoin from pyruvate, does not liquify gelatin, and does not ferment any of the 20E sugars (glucose, mannitol, inositol, sorbitol, rhamnose, sucrose, melibiose, amygdalin, L+arabinose); it does reduce nitrate to nitrate, but not to nitrogen gas.

As illustrated in Table 1a, *Serpens* spp., strain HBL-112 is distinct from *S. flexbilis* in that it gives a negative Voges-Proskauer reaction (VP) whereas the *S. flexibilis* gives a positive reaction. The Voges-Proskauer test is used to determine the bacteria's ability to metabolize pyruvate into acetoin, an intermediary glucose metabolite. Another clear difference is the ability of the *Serpens* spp., strain HBL-112 to migrate through soft (0.8%) agar plates. *S. flexibilis* migrates about 2 mm/hour whereas *Serpens* spp., strain HBL-112 migrates about 70–80% as fast. *S. flexibilis*' faster velocity through soft agar is matched by its higher growth rate in several medias including both Mueller Hinton broth and TSBA plates.

As shown in Table 1b, *Serpins* spp., strain HBL-112 gives the following reactions after a four hour incubation at TABLE 1b Comparison of Enzyme Reactions Related Bacterial Spp.

| Enzyme Composition | HBL Isolate, Strain #112 (1)* | ATCC Strain 29606 (1) | CYDLS Isolate (7) | CYDLS 1-9185 MED (1) | *Borrella* spp. (6) | *Leptospira interrogans* (12) | *Treponema* spp. (oral) (1) | *Serpulina* spp. (8) | Human Intestinal spirochetes (2) | Human & avian spirochetes (4) |
|---|---|---|---|---|---|---|---|---|---|---|
| Alkaline phosphatase | .5 | .5 | + | + | .5–2 | 2–4 | 2 | 3–5 | 1 | 1–2 |
| Esterase (C4) | 2 | 2 | + | + | 0–0.5 | .5 | .5 | 1–4 | 1 | 0–2 |
| Esterase lipase (C8) | 4 | 4 | + | + | 1 | 2–3 | .5–1 | 1–4 | 1 | 2 |
| Lipase (C14) | 1 | .5 | − | − | − | 1–2 | − | − | − | − |
| Leucine arylamidase | 3 | 4 | − | − | 2–4 | 3 | − | − | − | − |
| Valine arylamidase | .5 | .5 | − | − | − | .5–1 | − | − | − | − |
| Cystine arylamidase | − | − | − | − | − | .5–1 | − | − | − | − |
| Typsin | − | − | − | + | − | − | − | 0–2 | − | − |
| Chymotrypsin | − | − | − | + | − | − | − | 0–5 | − | − |
| Add phosphatase | .5 | .5 | + | + | 1–2 | 3 | 3–4 | 3–5 | 1 | 2–4 |
| Naphthol-AS-BI-phosphohydrolase | .5 | 1 | + | + | .5–1 | .5–2 | .5 | 0–2 | − | 0–.5 |
| α-galactosidase | − | − | − | − | − | .5–2 | − | 3–5 | − | .5–3 |
| β-galactosidase | − | − | + | − | − | 1 | 5 | 5 | 1 | 4 |
| β-glucuronidase | − | − | + | − | − | − | 5 | 3–4 | − | − |
| α-glucosidase | − | − | − | − | − | 1 | − | 2–5 | − | .5 |
| β-glucosidase | − | − | − | − | − | 1 | − | 3–5 | − | .5 |
| N-acetyl-β-glucosaminidase | − | − | + | − | − | − | 4 | − | − | .5 |
| α-mannosidase | − | − | − | − | − | − | − | − | − | − |
| α-fucosidase | − | − | − | − | − | − | 1 | − | − | − |

*(#) = # isolates or strains tested
− = no detectable enzyme reaction
.5 = <5 nanomoles enzyme
1 = 5 nanomoles enzyme
2 = 10 nanomoles enzyme
3 = 20 nanomoles enzyme
4 = 30 nanomoles enzyme
5 = 40+ nanomoles enzyme
+ = positive, but no level given 35–36° C. for the enzymes on the API-ZYM (bioMérieux) test strip after forty-eight hours aerobic growth on tryptic soy agar blood plates or in OTI broth or Mueller Hinton broth: weakly positive for alkaline phosphatase, acid phosphatase, naphthol-AS-BI-phosphohydrolase, and valine arylamidase; positive for C4 esterase and C14 lipase; strongly positive for C8 esterase-lipase and leucine arylamidase. The remaining eleven enzymes tested for on this strip were negative. Under the same growth conditions, *Serpens flexibilis* yields identical results.

Growth Parameters

*Serpens* spp., strain HBL-112, is capable of growth on solid phase standard tryptic soy blood agar (TSBA), Mueller Hinton, and chocolate agars (1.5–2% agar) or soft BSK-H (0.8% agar) plates under aerobic, anaerobic, 10% $CO_2$ (candle jar), and microaerophilic (BBL Campypak or Campypak Plus) conditions. With more oxygen, the organism has a slightly increased ability to migrate across the top of the agar surface. Growth on TSBA and BSK-H agar in these atmospheres occurs at 25° C., 30° C., and 35–36° C.; the temperature range is not however fully defined yet.

*Serpens* spp., strain HBL-112 is capable of growth suspended in liquid media in modified Eagle's media (MEM), Mueller Hinton broth, and fluid thioglycollate (PTG) media at 35–36° C. The addition of sterile donor horse serum at 2–5% (v/v) does not appear to affect growth in these medias.

*Serpens* spp., strain HBL-112 is capable of growth in standard microbiological liquid media at a pH range of 6.8 to 9.4, with optimum growth at approximately pH 7.4.

As used herein, the term, "*Serpens* spp. strain HBL-112" means bacteria of the *Serpens* spp. strain HBL-112 having the biochemical reactions set forth in Tables 1a and 1b.

The present invention encompasses the use of *Serpens* spp. strain HBL-112, *Serpens flexibilis*, or other *Serpens* species bateria, and/or an immunologically active portion thereof, and/or an antigenic epitope substantially cross-reactive with immunologically active portion(s) of *Serpens* species bacteria to provoke a protective immune response against PDD in ruminant species for the prevention and/or treatment of PDD.

A vaccine containing the bacteria or bacterin may be administered to animals having symptoms of PDD, or administered to animals having no signs of the disease.

The present invention provides methods and compositions for the prevention and/or treatment of PDD in ruminants, such as bovine, ovine and caprine species, comprising an effective amount of *Serpens* bacteria (live or killed) or an immunologically active portion thereof and an immunologically rational carrier, adjuvant, emulsifier and/or diluent herefor. Suitable *Serpens* bacteria are *Serpens* spp. strain HBL-112 and *S. flexibilis* bacteria, preferably *Serpens* spp. strain HBL-112. The killed bacteria may be conveniently prepared by propagation of pure culture *Serpens* spp. in conventional microbiological media, killing the bacteria by any suitable known method, and standardizing the antigenic mass to an appropriate CFU/ml equivalent. Where live vaccines are desired, the killing step is omitted, but the rest of the formulation proceeds as for the killed suspension. Where the purpose is to prepare a vaccine, suitable carrier(s), adjuvant(s), emulsifier(s), and/or diluent(s) may then be added to the (live or killed) bacterial suspension.

The composition of the present invention for the prevention and/or treatment of PDD may be prepared in a conventional manner by admixing the *Serpens* spp. killed or live bacterial suspension or an immunologically active portion thereof with an immunologically rational carrier, adjuvant, emulsifier and/or diluent, such as aluminum hydroxide or pharmaceutical grade mineral oil and emulsifier.

It is presently preferred to administer the composition of the present invention by subcutaneous administration, although parenteral or oral administration may be used as well. Oral compositions may incorporate the *Serpens* spp. bacteria or an immunologically active portion thereof or an antigenic epitope substantially cross-reactive with immunologically active portion(s) of *Serpens* spp. bacteria in drinking water or feed.

Although the dosage and regimen must in each case be adjusted, using professional judgment and considering the weight of the animal, generally the dosage will be from about $1\times10^8$ to about $1\times10^{11}$ CFU/ml, preferably from about $1\times10^9$ to about $1\times10^{10}$ CFU/ml based upon a 5 ml dose administered subcutaneously. In some instances, a sufficient therapeutic dose can be obtained at a lower dose while in others a larger dose will be required.

Although FIG. 1 shows vaccine doses administered at day 0, day 8 and day 35, it is presently preferred to administer two to three doses, the first at day zero, the second dose three to four weeks later and when desirable a third dose may be administered about three to four weeks after the second dose. Suitably, the doses will contain the same amount of bacteria or bacterin.

Parenteral administration can be effected utilizing liquid dosage unit forms such as sterile solutions and suspensions intended for subcutaneous, or intramuscular injection. These are prepared by suspending or dissolving a measured amount of the prepared bacterial suspension in a non-toxic sterile liquid vehicle suitable for injection, such as a sterile aqueous or oleaginous medium. Alternatively, a measured amount of the sterile bacterial suspension is placed in a sterile vial and sealed, or lyophilized and sealed. An accompanying sterile vial or vehicle can be provided for mixing prior to administration. Nontoxic salts and salt solutions can be added to render the injection isotonic. Adjuvants, stabilizers, preservatives and emulsifiers can also be added.

The present invention provides a method for the diagnosis of PDD and the detection of *Serpens* antibodies or *Serpens* antigens using conventional immunoassay methods. Sera from clinically affected or exposed but unvaccinated animals reacts with the *Serpens* antigen if it contains antibodies to the bacteria. Bound antibodies may be measured. Therefore the *Serpens* antigen can be used in a diagnostic test for screening of unvaccinated animals for prior exposure to the agent. Similarly, such a diagnostic test may also be used to assess the immune status of a vaccinated animal with respect to the *Serpens* antigen.

Conversely, antibodies made in an harvested from animals vaccinated with the *Serpens* bacteria may be utilized for the detection of *Serpens* bacteria.

A method for determining the presence of PDD antigen in a sample of ruminant tissue comprises administering a *Serpens* spp. bacteria or *Serpens* spp. bacterin and/or an immunologically active portion thereof and/or an antigenic epitope cross-reactive with *Serpens* spp. to the ruminant, harvesting the resultant antibodies or harvesting antibody producing cells and subsequently harvesting antibodies from those cells, binding the antibodies to binding partners and directly or indirectly measuring the binding reaction.

*Serpens* antigens, or anti-*Serpens* antibodies, or immunologically active fractions of either , may be used in a process designed for the concentration or purification of the coronary binding partner for use as a reagent.

A method for determining the presence of PDD antibodies in a sample of ruminant serum may suitably comprise contacting the sample with the *Serpens* spp. bacteria, preferably *Serpens* spp. strain HBL-112 bacteria, and detecting antibodies in said sample which bind to said antigen. A method for detecting PDD, or exposure to the *Serpens* bacteria thereof, via determining the presence of *Serpens* antibodies in a sample of ruminant serum may suitably comprise incubation of the sample with a solution containing at least one binding partner capable of binding to *Serpens* antibodies, and directly or indirectly determining the presence of conjugated binding partners in the sample.

The present invention uses serum for the samples and *Serpens* antigen as the respective binding partner, however the specific binding reaction may be utilized to detect either partner, hence other samples such as tissue sections, cell smears and parts thereof, or environmental samples, *Serpens* per se or fractions thereof may be studied using this method.

Either binding partner may incorporate one or more detectable markers such as a radioisotope, metal or fluorochrome, or may be detected indirectly, as though the use of conjugated enzyme with substrate detection.

Alternatively, in cases where neither of the primary binding partners incorporates a marker or other means for direct detection, secondary binding partnerships may be formed for subsequent detection either using *Serpens* group antigens or their complementary antibodies and/or anti-*Serpens* antibodies or through the use of binding partners which are not *Serpens* related, (such as avidin-biotin) but which may be used directly or indirectly for the detection of the primary binding partners.

Subsequent detection and quantification of the above markers, binding partnerships or other measurable medium may be by any conventional means appropriate to the methodology.

Alternatively, detection of *Serpens* in a sample can be made by means of directly or indirectly measuring physical features distinct to or characteristic of *Serpens*. Such measurements can include detection and measurements of compounds, or compound mixtures, including lipids, proteins or nucleic acids such as used in DNA amplification and identification techniques, or chromatographic separation and identification techniques such as gas or liquid chromatography.

In a further aspect of the invention, there is provided a diagnostic kit for use in performing the method according to the invention, which kit comprises *Serpens* antigen and one or more binding partners. The diagnostic kit may further include reagents required for sample preparation and optionally reagents for the detection of the bound antibody.

The present invention is illustrated in terms of its preferred embodiments in the following examples. All temperatures are in degrees Centigrade and all parts and proportions are by weight, unless otherwise noted.

EXAMPLE 1

Whole-cell *Serpens* spp. strain HBL-112, *Serpens flexibilis* or other *Serpens* spp. bacterins (killed cultures) are prepared by propagating bacterial cells in a standard microbiological media, killing the cells with formaldehyde, washing with sterile saline to remove cell debris, unused media components, bacterial waste products and the like, and suspending the bacterin in sterile phosphate buffered saline with 10% (v/v) aluminum hydroxide (adjuvant) and 0.01% thimerosal (preservative).

EXAMPLE 2

Whole-cell *Serpens* spp. strain HBL-112 or *Serpens flexibilis* or other *Serpens* spp. bacterins (killed cultures) are prepared by propagating bacterial cells in a standard microbiological media, killing the cells with formaldehyde, washing with sterile saline to remove cell debris, unused media components, bacterial waste products and the like, and emulsifying the bacterin in sterile phosphate buffered saline with 25% (v/v) pharmaceutical grade mineral oil and emulsifiers (adjuvant) and 0.01% thimerosal (preservative).

EXAMPLE 3

A non-virulent *Serpens* spp. or other apathogenic bacterial strain bearing cross-protective *Serpens* like antigens is propagated under standardized conditions (for example: using one of several conventional microbiological medias with a pH between 6.8 and 9.4, incubated at a temperature of approximately 25–37° C. under one of a variety of at atmosphere for a period of a few days to several weeks) ascertained to be a pure culture by suitable testing such as microscopic and colonial morphology, velocity through soft agar, characteristic motility under phase contrast microscopy, and/or biochemical testing and is then harvested. The harvested cells are washed, suspended in a sterile vehicle (for example, buffered saline) containing any conventional cryoprotectant typically used in vaccine manufacturing, filled into sterile vials and preserved by either freezing or lyophilization. The preserved material is thawed or reconstituted for administration either subcutaneously, orally or parenterally to ruminants at the appropriate dosage.

EXAMPLE 4

A total of 76 dairy cows with active, untreated lesions of PDD were enrolled in a treatment-based vaccine trial. Fifty animals were from the first milking string (highest producing cows), and twenty-six were from the hospital string. Since the hospital cows were likely undergoing treatment for mastitis which may have altered their immunological profile, only the first string cows were sampled and followed serologically.

All animals were stored for lameness and number of feet involved at the start of the trial; within lameness/foot groupings, each cow was randomly assigned to receive either vaccine or placebo for the trial. On the first day and approximately twice weekly thereafter each animal's feet were cleaned with plain water sprayed under moderate pressure from a hose-end sprayer and evaluated for presence, painfulness, number and size of PDD lesions; on each visit, milk production was recorded for evaluation as a possible covariate, and information on gestational status, age, lactation number and days in milk were obtained to evaluate possible covariates or confounders. Scoring was performed in a "blinded" fashion: the barn sheets did not show which animals were vaccinates and which were controls, and the number of enrolled animals precluded memorization of their status.

A 5.0 ml dose of vaccine or placebo was administered to each animal. The vaccine contained $2 \times 10^9$ CFU per ml of *Serpens* spp. strain HBL-112 bacterin suspended in sterile phosphate buffered saline with 10% (v/v) aluminum hydroxide and 0.01% thimerosal. The placebo contained no bacterin, bacteria or bactrial antigens, but was otherwise identical to the vaccine. The vaccine or placebo was administered to each enrolled animal on day 0, day 8, and day 35; initially, a two-dose closely spaced sequence was sought to determine whether or not the vaccine could be used therapeutically. Over the course of three to four weeks, clinical improvements were seen in many of the trial animals as shown in FIG. 1. Clinically, there seemed to be a "plateau"

in continued improvement, so the decision was made to administer a "booster" dose of vaccine at the fifth week in the trial. Part of the plateau was subsequently found due to the presence of persistent scar tissue which was being erroneously scored as wart tissue.

The reason the control group begins to show improvement after day 40 (FIG. 1), was that an oxytetracycline footbath was administered to the vaccinate and control cows. However, the vaccinates maintained their statistically significant advantage over controls in wart area reduction despite the improvement in controls attributable solely to the oxytetracycline footbath.

Three animals showing signs of lameness did not have evidence of lesions upon enrollment. When they did not develop lesions by eight weeks into the trial, they were dropped from the lesion analysis portions of the trial. Two of these animals did provide some useful information: neither was serologically positive on ELISA testing using *Serpens* spp. strain HBL-112 as the antigen, suggesting no prior exposure to the epitopes on this organism. That these non-lesion bearing animals did not recognize the *Serpens* spp. strain HBL-112 in an ELISA, while lesion-bearing nonvaccinates (controls) did, strongly suggests that a *Serpens* spp. bacteria is involved in the pathogenesis of the PDD lesion.

Figure 2:
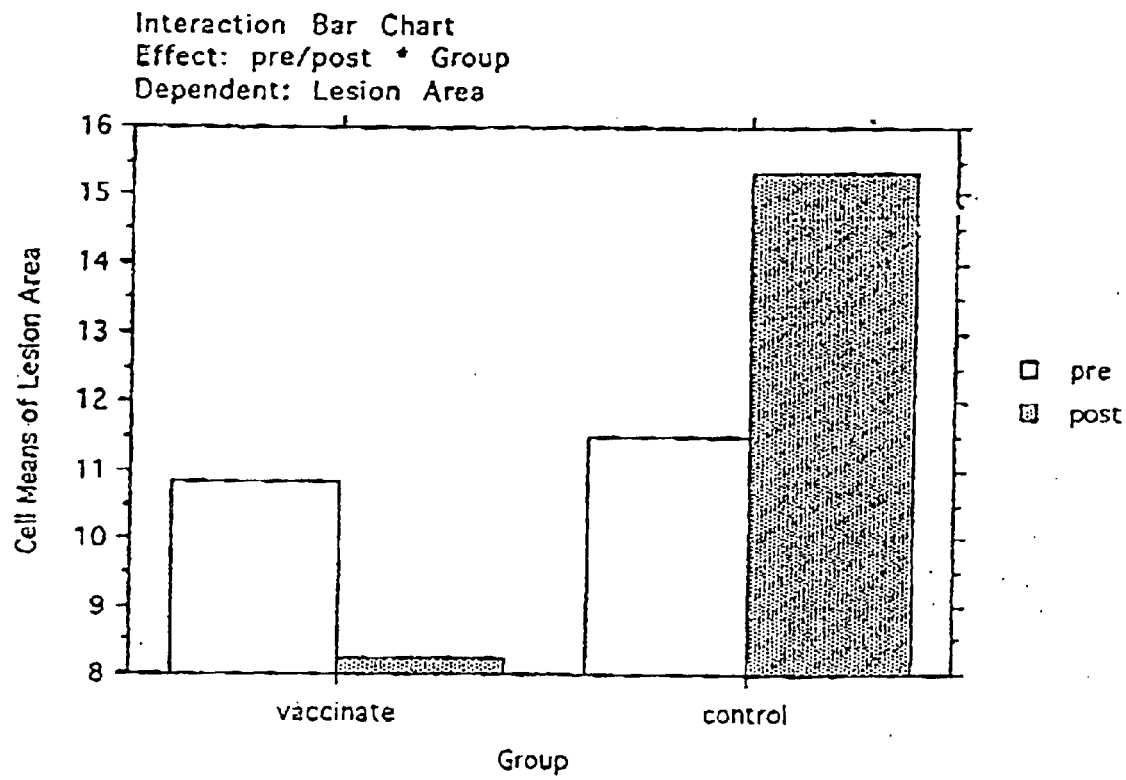
FIG. 2 is an interaction bar chart of the wart area by initial and postvaccination measurements (at day 49) in vaccinates and controls, with the associated Games-Howell post-hoc analysis demonstrating significance of the effect of vaccination.
Figure 3:
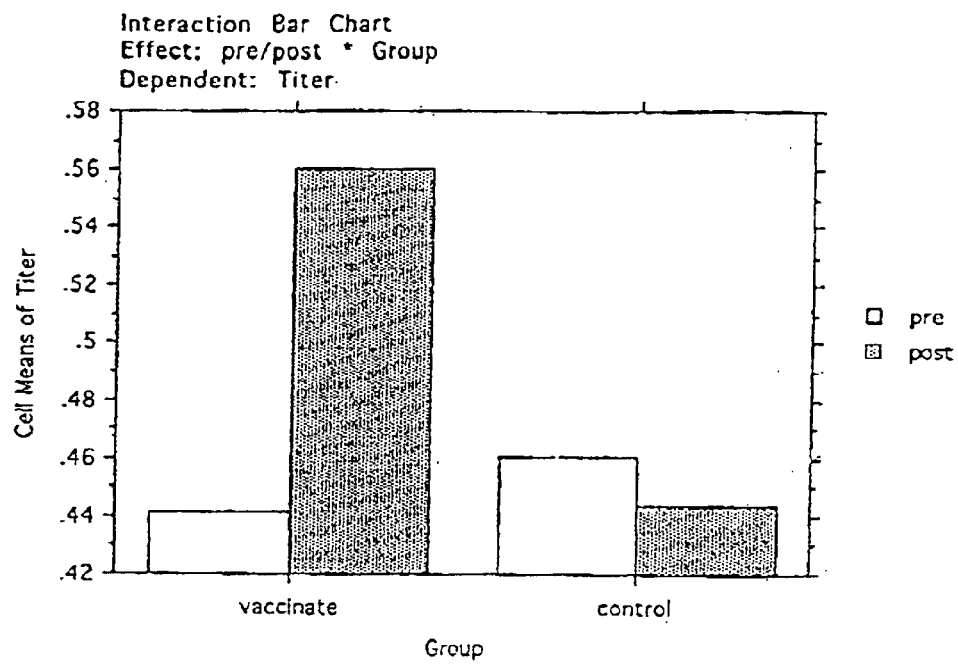
FIG. 3 is an interaction bar chart and Games-Howell analysis for serological titers in a random sample of about half of the enrolled animals by initial and postvaccination measurements (at day 49) in vaccinates and controls.
Figure 4:
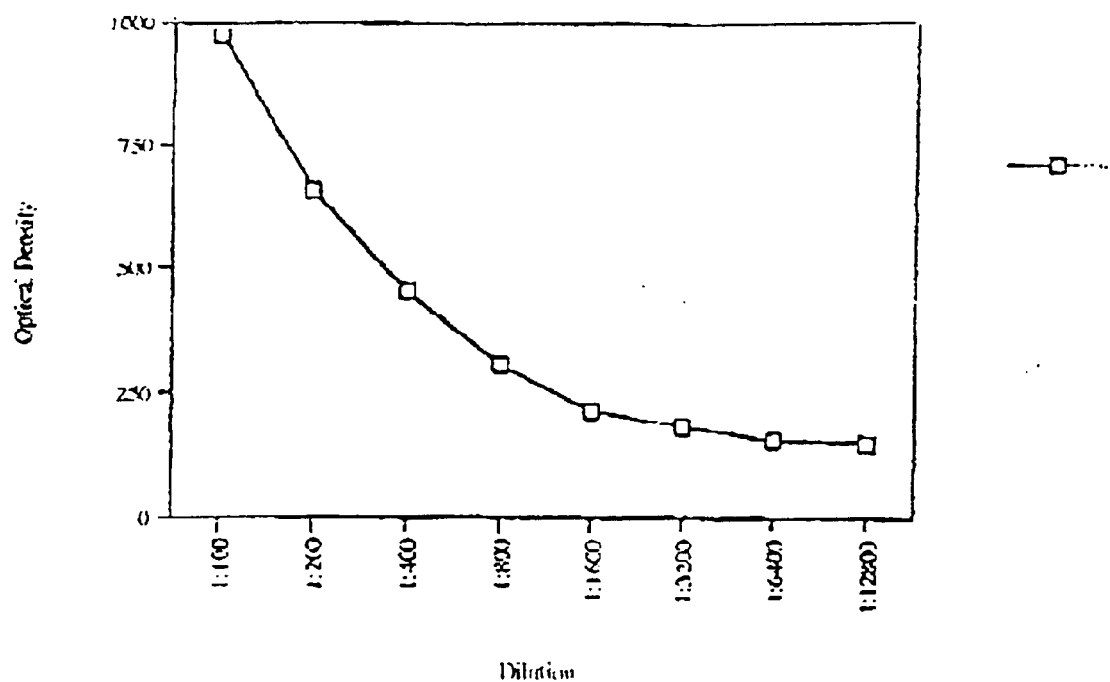
FIG. 4a is a graph showing a typical standard curve of a positive bovine serum sample titered in a capture ELISA.
FIG. 4b is a graph showing a standard curve of a competition ELISA using constant antibody and titered antigen.
Figure 4:
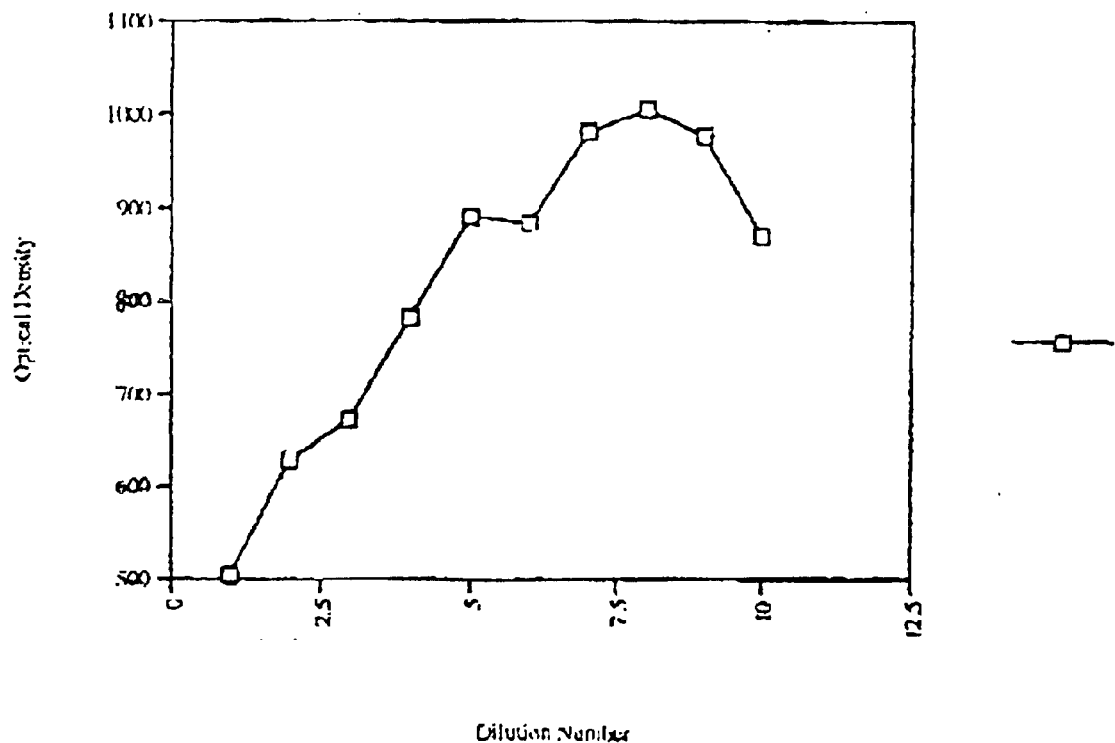

FIGS. 2 and 3 show effects occurring prior to any effect from the antibiotic footbath; the clinical effects seen in vaccinates (and lack thereof in controls) are thus attributable solely to the use of *Serpens* spp. strain HBL-112 bacterin. Further, limiting the data in the bar charts to result seen only through day 49 underreports the clinical improvement seen following the third dose of vaccine administered on day 36.

A total of forty-five animals were bled three times during the trial for measuring antibodies to PDD. Twenty-two serologically monitored cows were vaccinates, including two non-wartbearing animals; twenty-three animals were controls. As shown in FIG. 3, all wart-bearing animals (both vaccinates and controls) were seropositive to *Serpens* spp. strain HBL-112 on initial (prevaccination ELISA testing, indicating prior or concurrent exposure to the same or cross-reacting epitopes of HBL's vaccine strain. FIG. 3 further illustrates that while the control animals decreased in ELISA titer over the course of the trial, vaccinates showed titer increases, indicating that the vaccine was prompting an immunological response. Since this titer rise was detectable as early as eight days after the first (and at that time only) vaccination, it strongly suggests that the vaccine was prompting an anamanestic response in vaccinates, not simply a primary response (which typically requires 14–21 days to become detectable).

Generally, the absolute titer value was higher (albeit not significantly: 0.460 versus 0.441) among controls compared with vaccinates at the start of the trial, and remained the same or decreased over the course of the trial for twenty of twenty-three controls. The three controls showing small titer increases were also among those with the largest total lesion area during the trial; exposure to the agent in the lesions would account for the slight rise. Twenty-one of the twenty-one vaccinates showed a fairly large increase in titer (0.441 increased to 0.560) in response to vaccination; one animal showed a small decrease in titer.

Table 2 below, presents Type III Sums of Squares tables for dependent variables wart area and titer, showing statistically significant differences between vaccinates and controls in response to vaccination. While the herd as a whole improved significantly in lesion size (wart area) between the start of the trial and after 49 days (p value≈0.0420), the most significant effect is attributed to the vaccinates: p value= 0.0155 for the interaction of pre-post with vaccination status (=group). The change in titer seen in the herd as a whole between the start of the trial and at 49 days is solely attributable to the increases seen in vaccinates (p value for pre-post by group is highly significant at p value=0.0001 vs pre-post effects alone at p value=0.2682).

Table 3 below, presents a series of pre- and post-vaccination Means tables for the dependent variables examined in the analysis of the vaccine trial.

Of the factors measured, only total wart area shows statistically significant (@p<0.05) differences between vaccinates and controls. Vaccinates definitely did not develop as large lesions, nor did they remain lesioned as long as controls. See FIGS. 1–3.

TABLE 2

Type III Sums of Squares

| Source | df | Sum of Squares | Mean Square | F-Value | P-Value |
|---|---|---|---|---|---|
| Group | 1 | 185.306 | 185.306 | 2.005 | .1643 |
| Milk ProductionMilk Pro . . . | 1 | 5.012 | 5.012 | .054 | .8170 |
| Subject(Group) | 41 | 3789.260 | 92.421 | | |
| pre/post | 1 | 114.663 | 114.663 | 4.474 | .0420 |
| pre/post * Group | 1 | 166.998 | 166.998 | 6.516 | .0155 |
| pre/post * Milk Product . . . | 1 | 102.986 | 102.986 | 4.018 | .0533 |
| pre/post * Subject(Gro . . . | 33 | 845.727 | 25.628 | | |

Dependent: Lesion Area

Type III Sums of Squares

| Source | df | Sum of Squares | Mean Square | F-Value | P-Value |
|---|---|---|---|---|---|
| Group | 1 | .057 | 0.57 | 1.774 | .1902 |
| Milk ProductionMilk Produ . . . | 1 | .001 | .001 | .037 | .8492 |
| Subject(Group) | 41 | 1.310 | .032 | | |
| pre/post | 1 | .004 | .004 | 1.268 | .2682 |
| pre/post * Group | 1 | .099 | .099 | 35.402 | .0001 |
| pre/post * Milk Productio . . . | 1 | 8.995E–5 | 8.995E–5 | .032 | .8584 |
| pre/post * Subject(Group) | 33 | .092 | .003 | | |

Dependent: Titer

TABLE 3

Means Table
Effect: pre/post * Group
Dependent: Lesion Area

| | Count | Mean | Std. Dev. | Std. Error |
|---|---|---|---|---|
| pre, vaccinate | 20 | 10.850 | 7.252 | 1.622 |
| pre, control | 23 | 11.504 | 6.614 | 1.379 |
| post, vaccinate | 15 | 8.220 | 9.115 | 2.353 |
| post, control | 22 | 15.345 | 9.005 | 1.920 |

Means Table
Effect: pre/post * Group
Dependent: Lesion #

| | Count | Mean | Std. Dev. | Std. Error |
|---|---|---|---|---|
| pre, vaccinate | 20 | 1.850 | .988 | .221 |
| pre, control | 23 | 2.087 | 1.276 | .266 |

TABLE 3-continued

| | | | | |
|---|---|---|---|---|
| post, vaccinate | 15 | 2.333 | 1.397 | .361 |
| post, control | 22 | 3.000 | 1.574 | .335 |

Means Table
Effect: pre/post * Group
Dependent: Feet Affected

| | Count | Mean | Std. Dev. | Std. Error |
|---|---|---|---|---|
| pre, vaccinate | 20 | 1.750 | .967 | .216 |
| pre, control | 23 | 1.783 | .736 | .153 |
| post, vaccinate | 15 | 2.067 | 1.100 | .284 |
| post, control | 22 | 2.227 | .813 | .173 |

Means Table
Effect: pre/post * Group
Dependent: Lameness

| | Count | Mean | Std. Dev. | Std. Error |
|---|---|---|---|---|
| pre, vaccinate | 20 | 1.400 | .883 | .197 |
| pre, control | 23 | 1.261 | .810 | .169 |
| post, vaccinate | 15 | .533 | .516 | .133 |
| post, control | 22 | .818 | .733 | .156 |

Means Table
Effect: pre/post * Group
Dependent: Titer

| | Count | Mean | Std. Dev. | Std. Error |
|---|---|---|---|---|
| pre, vaccinate | 20 | .441 | .134 | .030 |
| pre, control | 23 | .460 | .123 | .026 |
| post, vaccinate | 15 | .560 | .173 | .045 |
| post, control | 22 | .444 | .130 | .028 |

EXAMPLE 5

The same antigen present in the vaccine, *Serpens* spp. strain HBL-112 bacterin, is also used in an ELISA test to monitor serological response to vaccination. Antigen (a 5% suspension of concentrated killed, washed whole cells, *Serpens* spp. strain HBL-112 bacteria, approximately $5\times10^8$ cells/ml, in a coating buffer, a sodium carbonate/bicarbonate buffer at pH 9.6) is placed in the wells of a 96-well microtiter plate overnight at room temperature. The plate is gently washed using a wash buffer, (a sodium phosphate buffer containing a detergent such as Tween or Triton (pH 7.5)). A bovine serum sample (primary antibody) is added and incubated in the plate at room temperature for one hour. The plate is gently washed again using wasH buffer to get rid of unbound antibodies. A secondary antibody made of an anti-cow antibody, such as from goat, conjugated with alkaline phosphatase is incubated in the plate for one hour at room temperature. The plate is gently washed again using wasH buffer. The plate is then incubated with p-nitrophenyl phosphate substrate in a 10% diethanolamine buffer (pH 9.8) and allowed to develop at room temperature until the maximum well O.D. is approximately 0.8 to 1.0, no stopping agents were used. The alkaline phosphatase enzyme attached to the secondary antibody converts the p-nitrophenyl phosphate substrate and turns the clear solution in the plate yellow. Binding of the primary antibody, secondary antibody and hence the strength of the O.D. reading is proportional to the amount of antibody present in the cow serum against the *Serpens* spp. strain HBL-112 antigen.

This method is essentially standard for ELISA, and any other ELISA method and numerous variations in this procedure would be expected to produce similar results. The procedure does differ from typical ELISA methods in that the incubation steps are done at room temperature. The purpose of this is only to reduce intrawell variation due to temperature induced edge effects.

Sera from unvaccinated animals binds to the *Serpens* spp. strain HBL-112 bacteria antigen if it contains antibodies for the bacteria.

EXAMPLE 6

It is often desirable to use a multivalent (multiple antigen) vaccine preparation to minimize the number of times an animal must be injected. Using a single pharmaceutical preparation which incorporates multiple antigens minimizes pain and risk of infection (abscesses at the injection site) for the animal, and decreases labor costs and risk of human injury (handling injuries and/or accidental self-injection) for the owner and their employees.

The same antigen used alone to produce the vaccines described in Examples 1 to 2 may also be used in combination with either antigens to produce a multivalent vaccine useful for treating and/or preventing other bacterial infections of ruminants in addition to PDD. The flexibility of the *Serpens* spp. vaccine schedule would permit virtually any other currently used ruminant vaccine antigen to be advantageously incorporated with *Serpens* spp. in a vaccine for simultaneous administration. Alternatively, the *Serpens* spp. antigen could be incorporated into any other ruminant pharmaceutical preparation administered by any method other than the intravenous route.

For example, strains of anaerobic bacteria such as members of the *Bacteroides* and/or *Fusobacterium* genera which are causative agents of the condition known as footrot in cattle and sheep may be incorporated with *Serpens* spp. antigens in a pharmaceutical preparation which when administered to susceptible ruminants will prevent both PDD and footrot. In another example, prevention of PDD in dairy cows may optimally require vaccination with *Serpens* spp. antigens during the non-milking "dry" period since the outbreaks of disease appear to peak during the first few months after lactation starts. Since many other vaccines are administered to the cow during this period to provoke high maternal antibody titers for transmission to the calf via colostrum, the *Serpens* spp. antigen may be advantageously administered to the cow with these object vaccine antigens during this dry period.

Alternatively, certain other antigens are known to have general immune-stimulatory properties, such as the "super-antigen" present in members of the *Staphylococcus* genus or the "core antigen" of certain members of the coliform bacteria such as the J-5 strain of *Escherichia coli,* when incorporated into vaccines with the primary antigen. In this case, incorporation of any suitable immune-stimulatory antigen with *Serpens* spp., strain HBL-112 or related antigen(s), results in a vaccine with enhanced immunoprophylactic properties.

What is claimed is:

1. An immunogenic composition comprising:

(1) an immunologically effective amount of a bacteria belonging to the genus *Serpens;* and (2) a veterinarily acceptable diluent or carrier.

2. The immunogenic composition of claim 1 further comprising an adjuvant.

* * * * *